Figure 1:
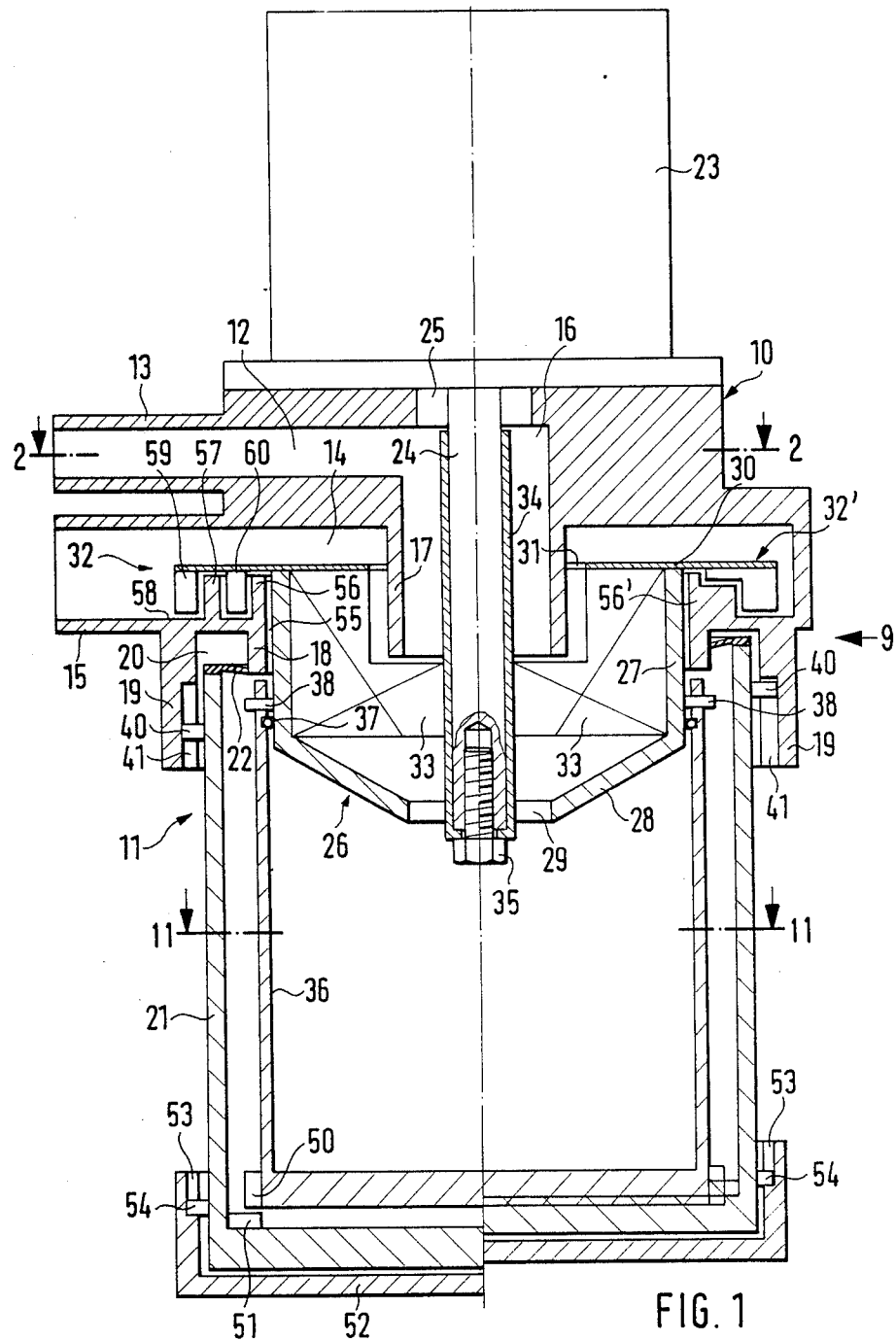

United States Patent [19]

Becker et al.

[11] Patent Number: 4,932,933

[45] Date of Patent: Jun. 12, 1990

[54] APPARATUS FOR SEPARATING FINE SOLID PARTICLES FROM WASTE WATER

[75] Inventors: Ernst Becker, Korb; Manfred Pausch, Darmstadt-Eberstadt; Horst Panzer, Hammersbach, all of Fed. Rep. of Germany

[73] Assignee: EMDA Fabrik elektromedizinischer and dentaler Apparate Georg Hartmann GmbH & Co. KG, Frankfurt am Main, Fed. Rep. of Germany

[21] Appl. No.: 265,391

[22] Filed: Oct. 31, 1988

[30] Foreign Application Priority Data

Oct. 31, 1987 [DE] Fed. Rep. of Germany ....... 3737002
Feb. 12, 1988 [DE] Fed. Rep. of Germany ....... 3804299

[51] Int. Cl.$^5$ ............................................... B04B 7/02
[52] U.S. Cl. ......................................... 494/62; 494/64; 494/67; 494/74
[58] Field of Search ..................... 494/60, 61, 62, 63, 494/64, 67, 74, 56, 31; 210/781, 782

[56] References Cited

U.S. PATENT DOCUMENTS 1,981,924 11/1934 Reese et al.
3,231,182 1/1966 Downey .............................. 494/60
4,353,499 10/1982 Simonds .............................. 494/60
4,356,959 11/1982 Rosander ............................ 494/62

FOREIGN PATENT DOCUMENTS 8603669 7/1986 European Pat. Off.
1380872 10/1964 France.
238684 8/1945 Switzerland.
395865 3/1965 Switzerland.
1507742 4/1978 United Kingdom.

Primary Examiner—Robert W. Jenkins
Attorney, Agent, or Firm—Toren, McGeady & Associates

[57] ABSTRACT

In a centrifuge device whose purpose is in particular the separation of amalgam from waste water generated in dentist' offices, the following is provided in order to improve the determination of the filling level in a collecting tank downstream from a centrifuge, to obtain better utilization of the container volume, to reduce the residual moisture in the separated solids, and to simultaneously eliminate the repumping means which operate between the collecting tank and the centrifugal. The collecting tank is detachably attached to a centrifuge drum and rotates together with the centrifuge, with measures being taken for separating the clean-water space from the centrifuge drum, there is also provided a transport container which can be detached from the device together with a collecting tank, which container can, when the collecting tank is in it, be closed by means of a cover which, when it is not in use, is detachably attached to the transport container. The device can also be designed in such a manner that a liquid/gas/solids mixture, generated, for example, in the oral cavity of a dentist's patient, can be fed to it simultaneously for the purpose of phase separation.

26 Claims, 10 Drawing Sheets

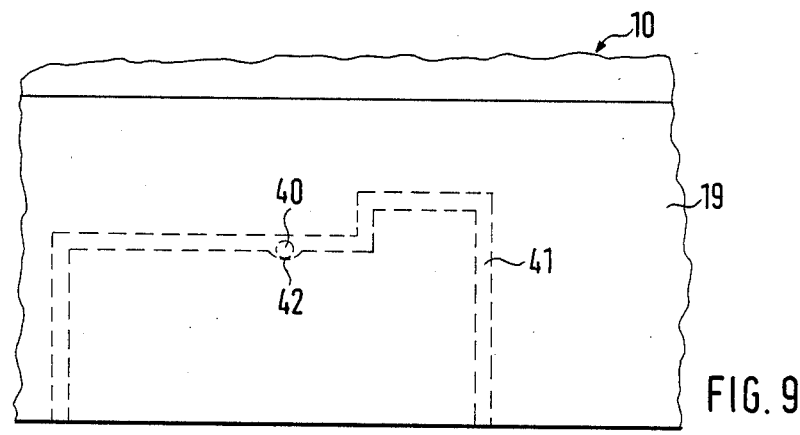
FIG. 9
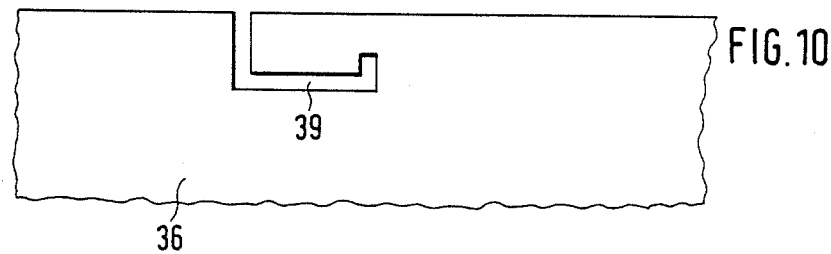
FIG. 10
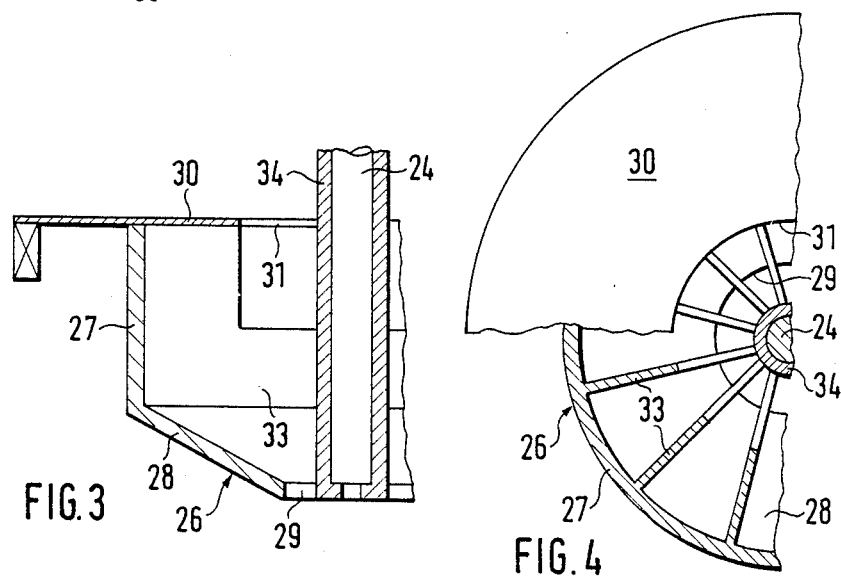
FIG. 3
FIG. 4

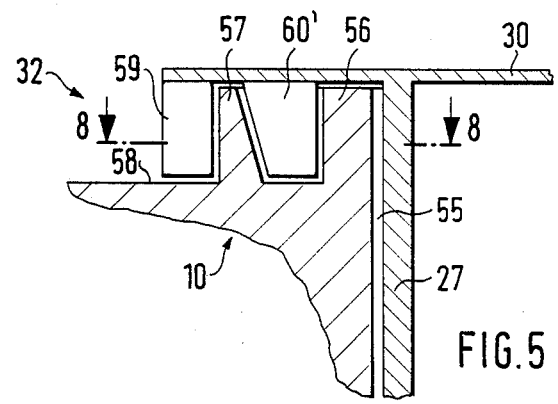
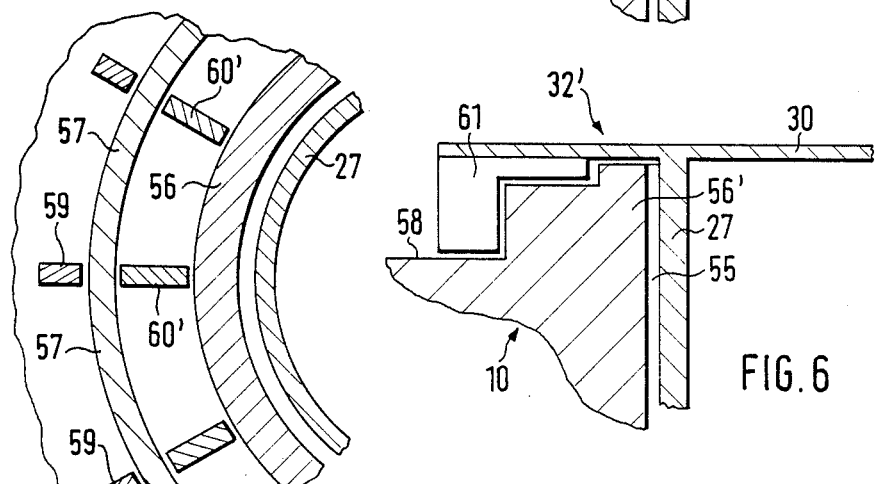
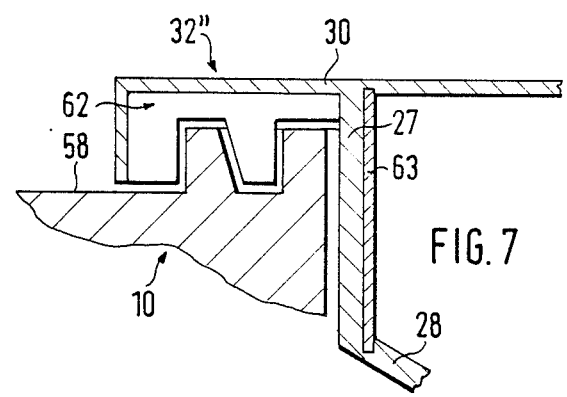

APPARATUS FOR SEPARATING FINE SOLID PARTICLES FROM WASTE WATER

The invention relates to a device for separating fine solid particles from waste water, in particular amalgam particles from the waste water of a dentist's office. Such devices including a centrifuge drum surrounding by a housing, the drum having a peripheral wall, a conic drum bottom having a central orifice and being connected to the drum wall so as to project downwardly and a ring-shaped barrier flange carried by the upper free end of the peripheral wall of the drum so as to extend radially inwardly and form a limit of an overflow opening through which the inside of the centrifuge drum communicates with a discharge space for clean water, which space is located in said housing. A drive shaft of a motor is attached to the housing, which drive shaft carries the centrifuge drum, and an inlet tube which surrounds the drive shaft concentrically at radial distance, is firmly attached to the housing, passes through the overflow opening with radial play and communicates with a duct located in the housing for intake of waste water, and with the interior space of the centrifuge drum. A collecting tank for the separated solid particles is detachably attached and communicates through the orifice with the interior space of the centrifuge drum.

In known devices of this kind (e.g. German Disclosure Document No. 35 42 115, FIG. 7) the collecting tank for the solid particles is connected to the housing in such a manner that, when the centrifuge drum is standing still, it is filled, through the central orifice in the bottom of the drum, with separated solid particles, starting at the center of the tank. This results in poor utilization of the storage volume provided in the collecting tank. In addition, in the known devices it is necessary to provide special means at the lower end of the hub of the centrifuge for pumping the water flowing into the collecting tank back into the centrifuge drum when the centrifuge is started. Another source of difficulties in the known devices is the collecting of information on the filling level of the collecting tank, because reliable information requires sufficient sedimentation of solid particles in the collecting tank.

It is the purpose of the invention to provide a device of the above-mentioned type, in which the utilization of the storage volume of the collecting tank and the collection of information on the filling level are improved while at the same time no special means for pumping the water from the collecting tank are required.

This object is achieved by a device of the above-mentioned type wherein the collecting tank is detachably and in a sealed manner attached to the centrifuge drum in such a manner that it cannot rotate relative to same, and the barrier means is provided with separate housing space adjoining the external periphery of the peripheral wall of the drum from the discharge space for clean water.

According to the basic idea of the present invention, the collecting tank participates in the rotation of the centrifuge drum, so that the centrifugal force will act also on the separated solid particles, which have entered the collecting tank under the influence of gravity while the centrifuge drum is standing still, and on the water in the tank. The separated solid particles are therefore deposited in a ring-shaped manner on the inner wall of the rotating collecting tank, with the layer thickness increasing with operating time, while the water entering the collecting tank also forms a ring on the inside whose thickness is limited by the diameter of the central orifice in the bottom of the drum. An excess of water is pushed upwards through the orifice into the centrifuge drum as a result of centrifugal force and without any additional pumping or similar equipment being required. In this manner a well-defined laminar structure of the separated solid particles in the collecting tank, and consequently a good utilization of its storage volume, are achieved. The well-defined laminar structure also makes it much easier to obtain exact information on the filling level. In addition the layer of solid particles precipitated in the collecting tank is greatly densified and as a result the residual moisture in the sediment is low, which in turn facilitates recovery of the precipitated solids. The barrier means ensure when the centrifuge is in operation and also when it is standing still that clean water from the discharge space cannot flow to the exterior of the centrifuge drum.

By placing the collecting tank within a transport containers which surrounds the collecting tank so as not to touch it and which has an opening by which it is attached to the housing in a sealed and detachable manner, it is ensured in an advantageous manner that the collecting tank participating in the rotation is covered toward the outside by the transport container which does not participate in the rotation, and that after it has been replaced and its contents are protected for transportation to a waste treatment facility. The seal between housing and transport container ensures that any clean water which, in spite of the barrier means, penetrates into the housing space at the outside wall of the drum cannot escape to the outside from the device.

In order to detachably fasten the collecting tank and the centrifuge drum to each other, a screw connection may be established between these parts, but preferably a bayonet lock is used which can be unlocked by lifting and rotating the collecting tank. This design also offers, together with a bayonet lock for attaching the transport container to the housing the advantageous possibility to detach the collecting tank and the transport container simultaneously and jointly from the device. All that is required for this purpose is to lift and rotate the transport container. When this is done the bayonet locks of both containers are released so that both containers can be pulled out downwards to release the engagement with the housing and the centrifuge drum, respectively.

By providing a catch for the lock of the transport container, it is ensured that it is impossible to bring the transport container inadvertently into a position which permits lifting. The catch provided here locks the transport container in a defined position on the housing.

In a further embodiment, a cover is provided for closing the transport container with the collecting tank inside. A convenient storage is provided for the cover when it is not in use.

In yet another embodiment a seal is provided in an advantageous manner on the collecting tank for sealing the collecting tank against both the housing and the cover when it is in place.

In an advantageous further development of the invention the barrier means which separate the discharge space containing the clean water from the housing space adjacent to the peripheral wall of the drum and thus also from the gap space between the collecting tank and transport container has at least one closed ring-shaped wall which is concentric with the centrifuge drum and protrudes upwards from the bottom surface of the discharge space for clean water, and at least one circle, also concentric with the centrifuge drum, of vanes which are radially oriented and adjoin the ring-shaped wall in such a manner that a narrow gap is formed. The barrier flange also extends radially outwards from the peripheral wall of the drum beyond the ring-shaped wall, of which at least one is present, and the vanes are attached to the barrier flange in such a manner that they protrude downwards. When the centrifuge drum rotates the vanes participate in this rotation with the same angular velocity because they are fastened to the barrier flange and move the clean water discharged from the overflow opening radially outwards, thus creating an effective dynamic seal. When the centrifuge stands still the ring-shaped wall acts as a barrier wall within the discharge space and prevents the clean water from flowing in the reverse direction, even if the water level in the discharge space is high.

Useful embodiments of the barrier means discussed above include: (1) two ring-shaped walls and two circles of vans engaged therewith; (2) one ring-shaped wall having outer steps, and vanes with a corresponding step shape; and, (3) vanes extending to the peripheral wall of the drum.

In further pursuit of the idea of the invention, the desirable possibility to determine the exact filling level in the collecting tank which is offered by the invention is put into practice by providing at least two channels on the collecting tank which are positioned opposite each other in pairs, are directed inwards, have identical dimensions and consist of material which is transparent to light. If desired, the transport container is transparent to light in at least two areas located opposite each other and, in a manner known per se, a light-sensing system is fastened to the frame of the centrifuge for the purpose of determining the filling level, with the optical axis of said light-sensing system being lined up with said channels. Here the depth of the channels determines the permissible level in the collecting tank, i.e. the permissible thickness of the layer of solid particles which have been separated and deposited on the wall of the collecting tank by the action of the centrifugal force. As soon as the layer has become so thick that the opposing surfaces of the channels are covered by solid particles an optical and/or acoustic signal is triggered with the aid of the electric eye, which indicates that the collecting tank has to be replaced.

Instead of or in addition to the above-described level measurement by means of a sensor, it is also possible, in further pursuit of the idea of the invention, to determine the filling level, by evaluating the starting torque of the motor, which is made possible by the fact that the collecting tank participates in the rotation.

As a result of the choice of the inside radius of the collecting tank to be greater than the inside radius of the peripheral wall of the drum the sediment is densified even more because of the comparatively higher circumferential velocity at the collecting tank wall and the resulting stronger action of the centrifugal force on the separated solids.

In a further embodiment of the device according to the invention, this device is designed in such a manner that liquid/solids mixtures and liquid/gas/solids mixtures can be fed to it simultaneously in order to separate the solid particles and the gaseous phase from liquids. In this design even large quantities of liquid do not cause a shut-off of the gas exhaust of the device and no complicated valve control systems are required. With regard to the preferred use of the device in dentists' offices this means that the device can be used to receive and process the contaminated waste water from the cuspidor bowl, which contains solids, and simultaneously process the liquid/gas/solids mixture sucked from the oral cavity, for the purpose of separation or phase separation, respectively.

This is achieved by providing a suction tube concentrically with the drive shaft and permanently attached to the housing, whose lower open end extends into the centrifuge drum and forms the limit of a suction space surrounding the drive shaft, which space can be connected to a source of reduced pressure. A separating tube is provided between the suction tube and the inlet tube and concentrically to them, which is located in the housing and attached to the centrifuge drum in such a manner that it cannot rotate relative to the latter, whose upper open end communicates with the intake duct for a liquid/gas/solids mixture, whose lower open end extends into the centrifuge drum and which forms, together with the suction tube, a ring-shaped space. The upper end of the separating tube passes rotatably through a sealing ring fastened to the housing which seals the intake duct for waste water against the intake duct for liquid/gas/solids mixtures. The separating tube comprises at its lower end a separating flange extending outwards which, when the centrifuge is in operation, dips with its entire periphery into a liquid layer formed on the peripheral wall of the drum. In the device according to this design the sucked-off liquid/gas/solids mixture is separated into a liquid/solids phase and a gaseous phase by the centrifugal action of the separating tube which participates in the rotation and which seals off, by means of the separating flange dipping into the water ring of the centrifuge drum, the space in which the pressure is reduced from the outside pressure. The liquid/solids phase flows downwards along the inner wall of the separating tube and then outward along the separating flange and then flows into the water ring of the centrifuge drum from which the solids move to the peripheral wall of the drum, while the liquid phase flows, past the barrier flange with a weir-like action, into the discharge space for clean water. The gaseous phase, on the other hand, is pushed toward the center of rotation and flows downwards along the suction tube until it is deflected by 180° at the lower end of said tube and enters the exhaust space.

Due to the design of the device in accordance with the invention, the gaseous phase is reliably separated and discharged through the source of reduced pressure, even if large volumes of waste water arrive simultaneously in the device, particularly if the cuspidor bowl is emptied and/or from the suction system.

By having the suction tube communicate at its upper end with a suction duct tangentially connected to the suction space, the formation of a gas cyclone in the exhaust space is assisted. Small drops of liquid carried along by the gas flow are separated from the gas flow by the cyclone effect at the point where the 180° deflection takes place and are carried outwards outside, away from the center of rotation.

By providing several acceleration vanes at equal distances from each other in a ring-shaped space between the suction tube and the separation tube, which vanes are attached to the separation tube and extend radially to a point at a distance from the suction tube, and connecting the intake duct for the liquid/gas/solids mixture tangentially to the ring-shaped space between the suction tube and the separating tube the separating action of the device for liquid/gas/solids mixtures coming from the suction system is increased.

In a further embodiment, the accelerating vanes are made in one part with guiding vanes which connect the centrifuge drum with a hub sleeve placed on the drive shaft in such a manner that these parts cannot rotate in relation to each other.

In still another embodiment, the intake duct for waste water is tangentially connected to a ring space-shaped inlet chamber whose outside limits are formed by the housing and the inlet tube.

In yet an additional embodiment, the inside limits of inlet chamber are formed by the separating tube which passes through it coaxially.

In a further design of the device a separating flange divides the centrifuge drum into two sections, one above the other, the upper one of which is used for separating the solids from the waste water, while the lower one is used for separating the solids from the liquid carried along by the exhausted liquid/gas/solids mixture. Accordingly, the upper section is under the same pressure as the surroundings, while the pressure in the lower section is reduced. When the centrifuge drum stops the pressures are equalized. The separated solids coming from the upper and lower section are carried downwards through the orifice in the centrifuge drum by the action of gravity.

In still a further arrangement, the housing is composed of a lower housing and an upper housing, with the lower housing comprising the inlet chamber for waste water, the inlet tube, the intake duct for waste water, the discharge space for clean water and the centrifuge drum with the separating tube, while the housing comprises the suction duct, the intake duct for the incoming liquid/gas/solids mixture and the suction tube protruding therefrom, and the drive shaft and the hub sleeve pass through the upper and lower housings, with the hub sleeve passing through a housing seal in the upper housing, which seals off the reduced pressure from the outside.

In a further embodiment the intake duct for waste water, one discharge duct for clean water, the suction duct and the intake duct for the liquid/gas/solids mixture all lead, one above the other, to one side of the device, this further improves the compactness of the device according to the invention and makes it easier to connect the devices to the corresponding piping.

In an additional arrangement the suction tube in the area of the intake duct for the liquid/gas/solids mixture is closely surrounded by an enveloping tube whose lower end extends into the ring-shaped space between the suction tube and the separating tube and is connected through the accelerating vanes with the separating tube in such a manner that it cannot rotate in relation to the latter. This further improves the separating action of the device for sucked-off liquid/gas/solids mixtures because immediately after entering the device the mixtures make contact with the cover tube which rotates at the same speed as the centrifuge and flings the mixture toward the outside as seen from the center of rotation. It is therefore completely impossible for the liquid and solid parts of the mixture also to flow along the suction pipe, as the entering mixture is immediately repelled by the rotating cover tube and transferred to the rotating separating tube which effects separation of the gaseous phase. This design ensures that the gaseous phase exhausted from the device is completely dry.

When the ring-shaped space is designed in such a manner that between the suction tube and the separating tube its cross section continually decreases in the flow direction of the liquid/gas/solids mixture, a nozzle effect is created in the ring-shaped space for the liquid/gas/solids mixture, i.e. the flow is accelerated.

Figure 2:
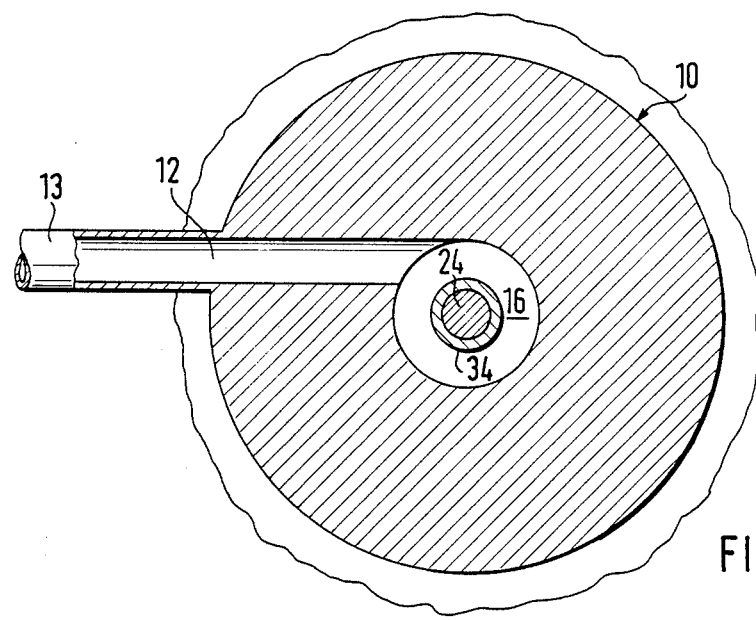
Figure 11:
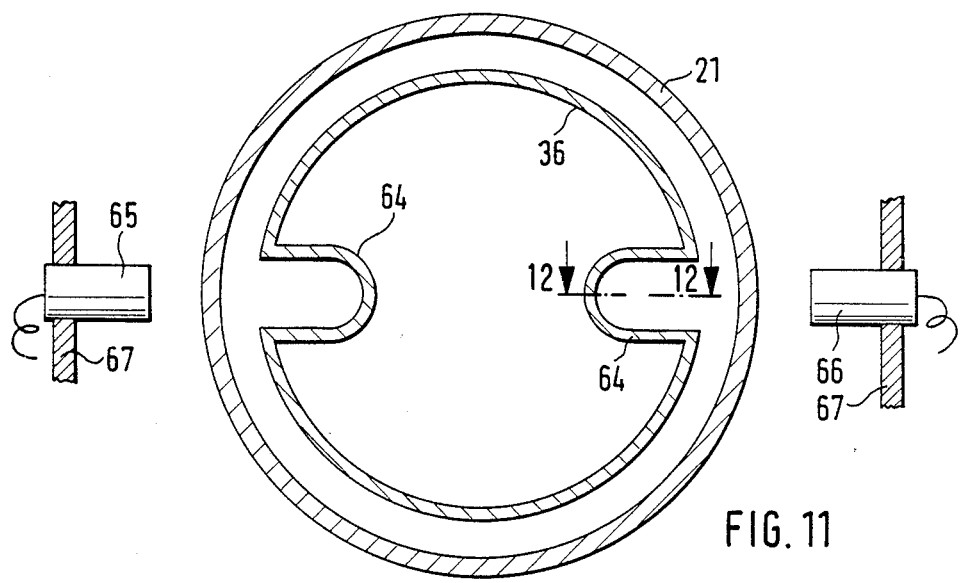
Figure 12:
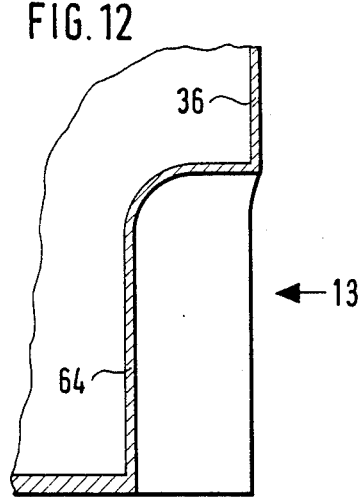
Figure 13:
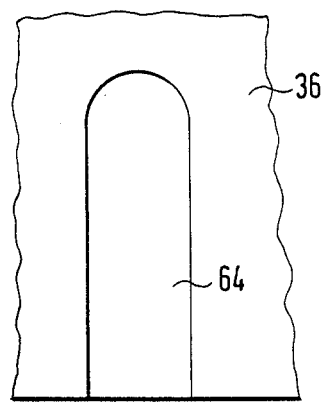

Additional details of the invention Will be explained below with the aid of drawings which show several embodiments, partly in a schematic manner. In these drawings:

FIG. 1 shows a vertical section through the device for separating fine amalgam particles from the waste water generated in a dentist's office, FIG. 2 a partial view of the cross section through the housing of the device along line II—II in FIG. 1, FIG. 3 a partial view of a vertical section through the centrifuge drum, FIG. 4 a partial top view of the centrifuge drum of FIG. 3, FIG. 5–7 partial views of vertical sections through various embodiments of the barrier means, FIG. 8 a partial view of a section through one of the embodiments along line VIII—VIII in FIG. 5, FIG. 9 a partial view of a housing detail corresponding to arrow IX in FIG. 1, FIG. 10 a partial side view of the upper part of the collecting tank with a bayonet-lock slot, FIG. 11 the cross section through the collecting tank and the transport container along line XI—XI in FIG. 1, FIG. 12 a partial view of a vertical section through the collecting tank along line XII—XII in FIG. 11, FIG. 13 a partial side view of the collecting tank according to arrow XIII in FIG. 12

Figure 14:
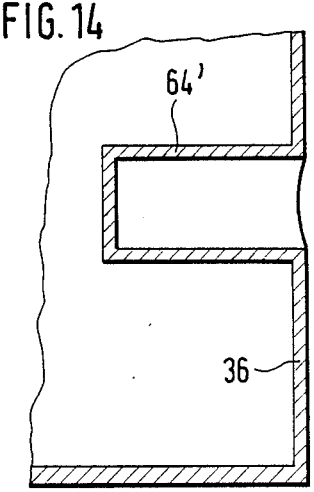
Figure 15:
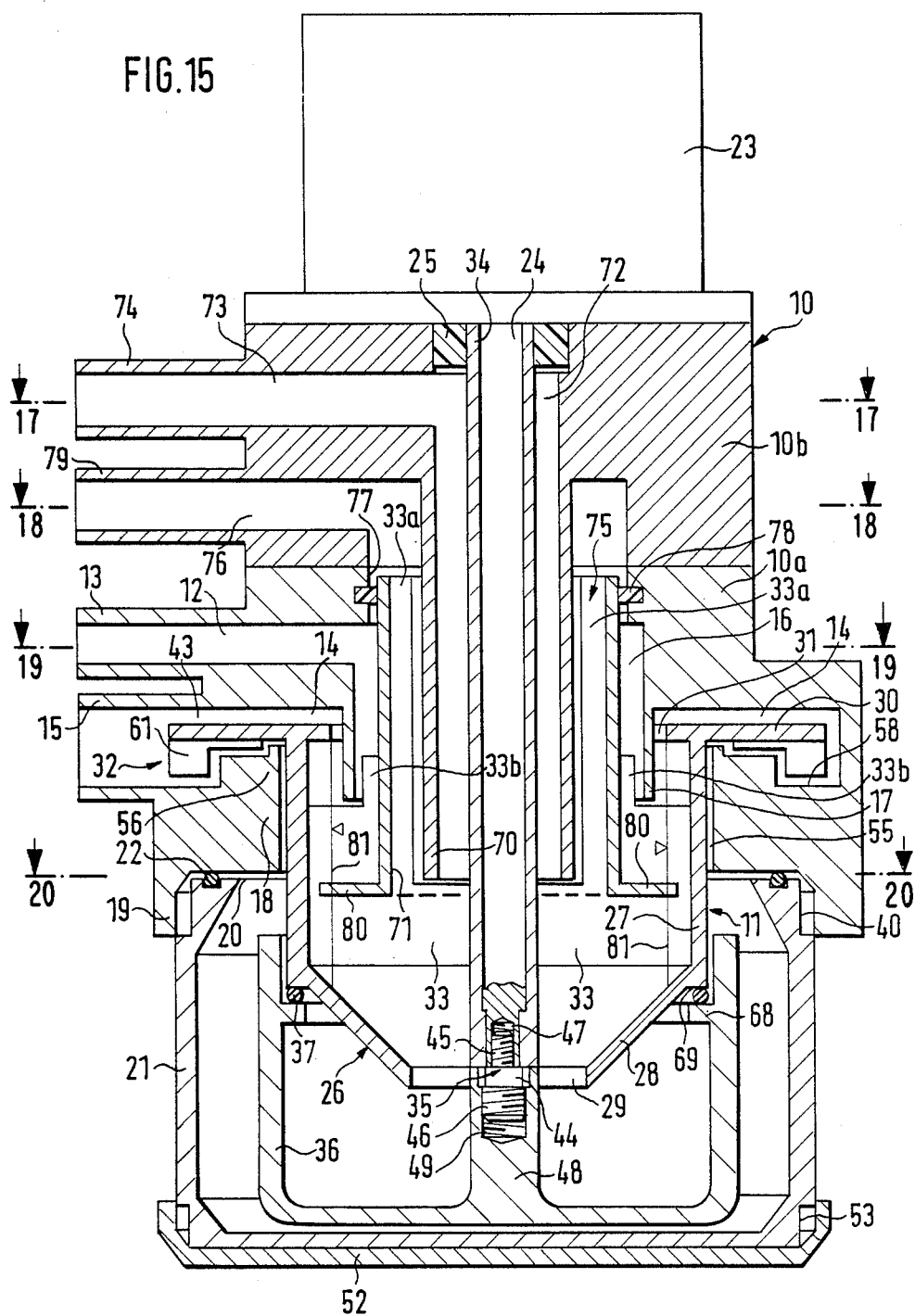
Figure 16:
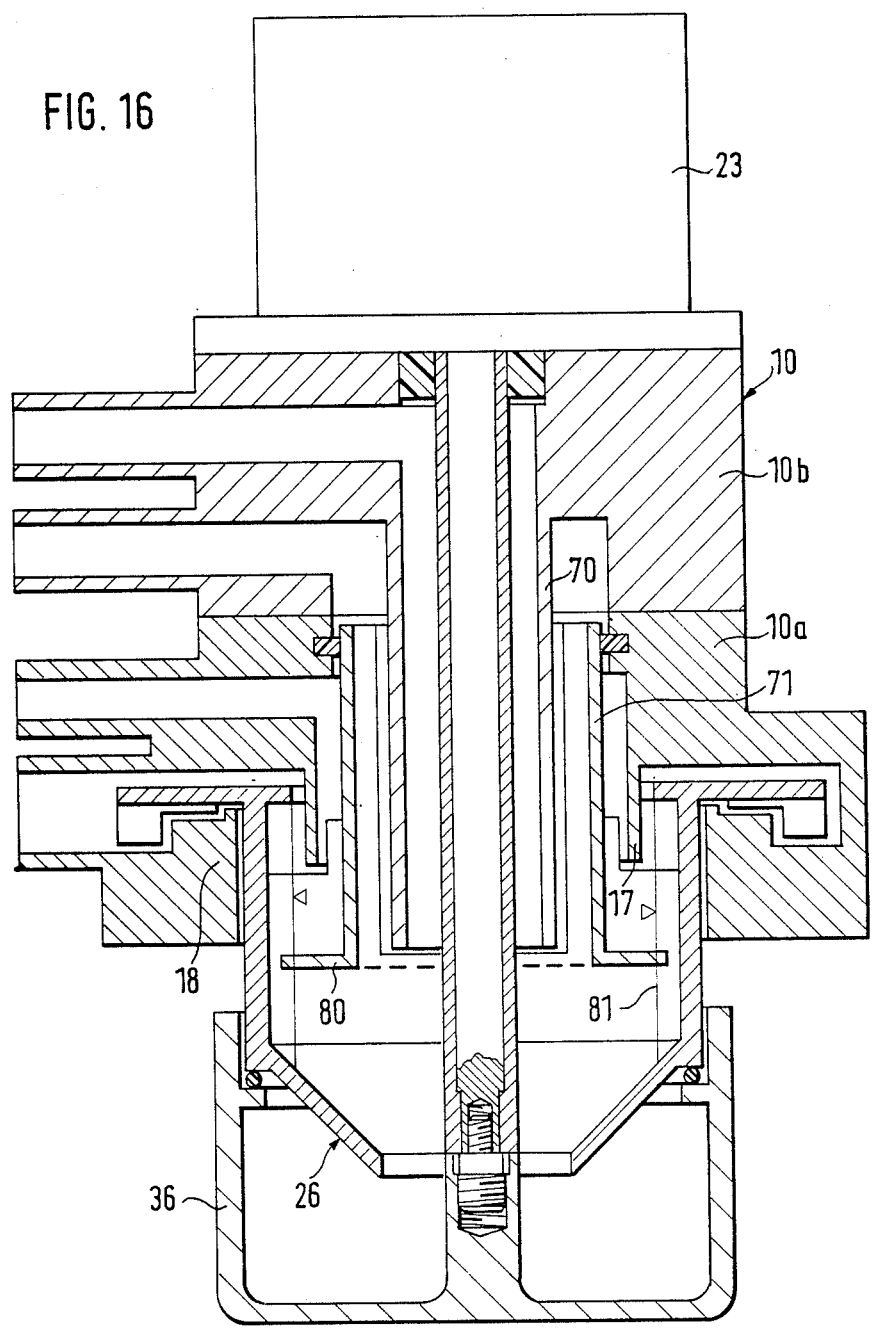
Figure 17:
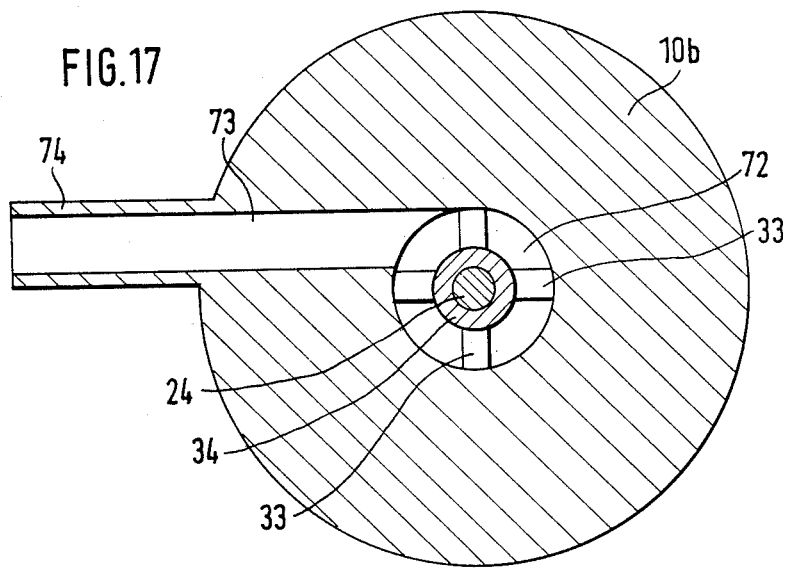
Figure 18:
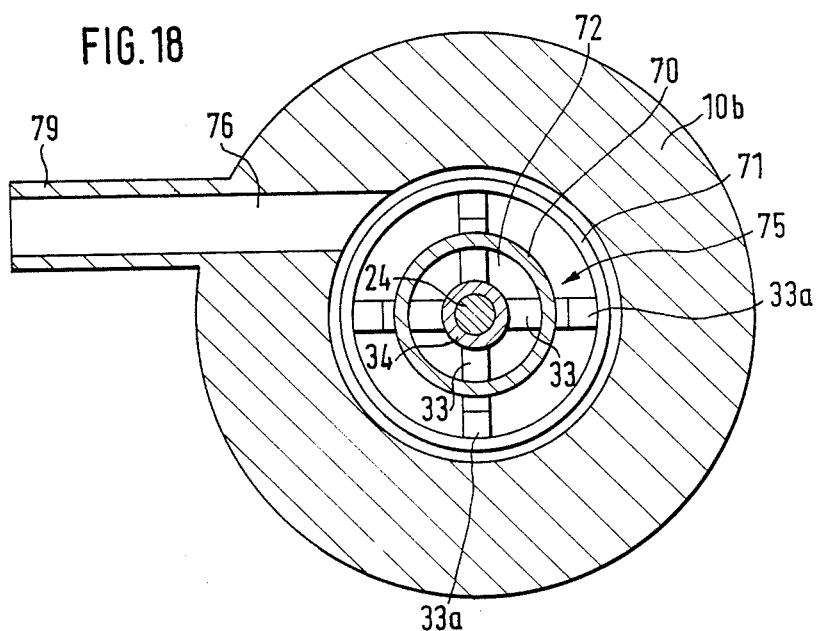
Figure 19:
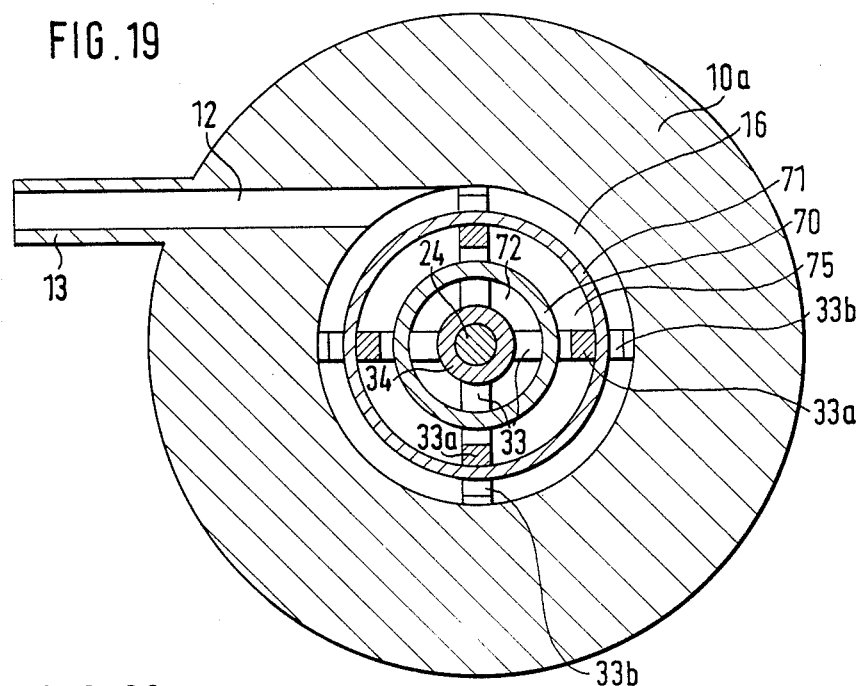
Figure 20:
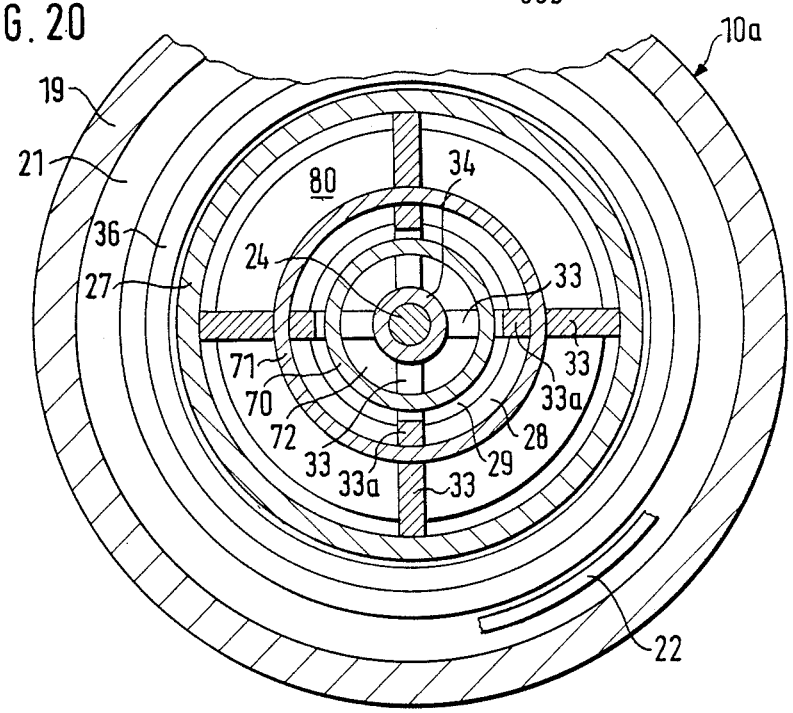
Figure 21:
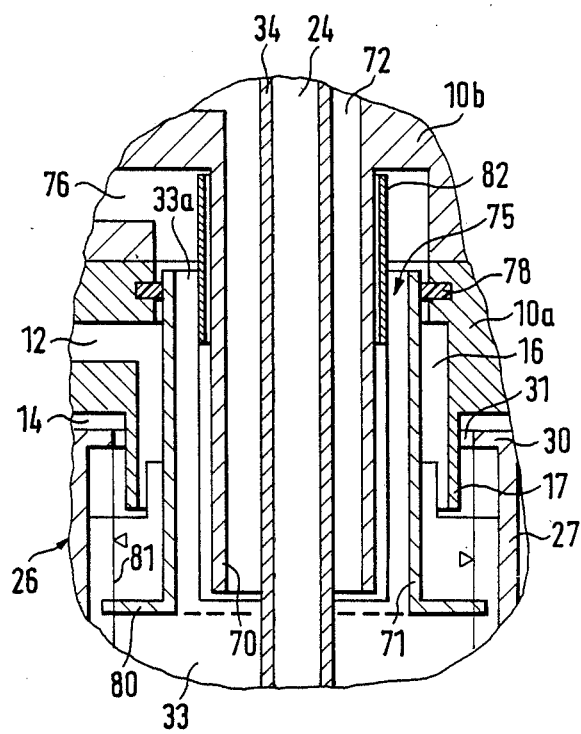

FIG. 14 a vertical section through an embodiment of the collecting tank, similar to FIG. 12, FIG. 15 a vertical section through the device for the simultaneous separation of solids, such as amalgam particles, from the waste water generated in a dentist's office and separation of a mixture sucked from the mouth of the patient, in a first embodiment, FIG. 16 a vertical section, essentially corresponding to FIG. 15, through a second embodiment of the device, FIG. 17 a cross section through the device along line XVII—XVII in FIG. 15, FIG. 18 an additional cross section through the device along line XVIII—XVIII in FIG. 15, FIG. 19 another cross section through the device along line XIX—XIX in FIG. 15, FIG. 20 again a cross section through the device along line XX—XX in FIG. 15, FIG. 21 the central section, broken off on all sides, of the device according to FIGS. 15 and 16, with a modification of the device.

The device shown in FIG. 1 for separating amalgam particles from the waste water generated in a dentist's office is, to the left and the right of the centerline of the device and in a manner which will be described below, partly designed differently and partly shown in different positions. The housing of the device carries as a unit the reference numeral 10, while the centrifuge as a unit is carrying reference numeral 11.

Intake fitting 13 is attached to intake duct 12 which is located in housing 10 in a direction transverse to the centerline of the device. Ring-shaped discharge space 14 for the clean water coming from centrifuge 11 is located below intake duct 12, and discharge fitting 15 is attached to said discharge space 14. As shown in FIG. 2, intake duct 12 leads tangentially into inlet chamber 16 which is concentric with the centerline of the device and to which is connected inlet tube 17 leading downwards. Inlet tube 17 forms the inside limit of ring-shaped discharge space 14 and reaches into casing wall 18 of housing 10, which casing is concentric with the centerline of the device and essentially encloses centrifuge 11.

An external ring-shaped wall 19 which extends further downward is provided on the housing at a radial distance from the cylindrical casing wall 18. Said wall 19 forms the outer limit of the ring-shaped receiving space 20 which is open toward the bottom and whose inner limit is formed by casing wall 18. The upper end of transport container 21, which is detachably fastened to housing 10 in a manner described below, extends into receiving space 20. Transport container 21 has the shape of a cylindrical cup and carries on the edge of its opening the lip seal 22 which makes contact with the cylindrical outer surface of casing wall 18 in such a manner that a seal is formed but that said lip can be moved up and down, as is shown by a comparison of the left and right half of FIG. 1.

Electric motor 23 is attached by a flange to the top of housing 10 in such a manner that its principal axis is in line with the centerline of the device. Drive shaft 24 of electric motor 23 passes through housing seal 25 and ends below inlet tube 17. Drive shaft 24 carries in the manner described below a centrifuge drum which is attached to it in such a manner that it cannot rotate in relation to said shaft. The complete centrifuge drum is designated by reference numeral 26.

Centrifuge drum 26 comprises peripheral wall 27 and conical bottom 28 which adjoins said wall at its lower edge, with said bottom ending in orifice 29. Orifice 29 is of circular shape and concentric with the centerline of the device. At the free end of peripheral wall 27 of the drum and attached to it firmly and tightly, and for example forming one piece with it, there is located barrier flange 30 in the shape of a circular ring which on the inside forms the limit of overflow opening 31, also in the shape of a circular ring. The outside surface of inlet tube 17 forms the inner limit of overflow opening 31. Barrier flange 30 also extends radially outward from peripheral wall 27 of the drum in order to permit the placement of barrier means which will be explained in detail below. These barrier means are shown with different shapes in the left and right halves of FIG. 1 and carry reference numerals 32 and 32′. By means of a plurality of radially oriented guiding vanes 33, centrifuge drum 26 is rigidly attached to hub sleeve 34 which is slid onto drive shaft 24 and fastened to the latter by screw 35 so that centrifuge drum 26 and all parts rigidly attached to it are carried by drive shaft 24 in such a manner that they cannot rotate relative to said shaft. FIGS. 1, 3 and 4 show that the guiding vanes 33 extend between the inner surface of peripheral wall 27 of the drum and the hub sleeve. In the embodiment shown the vanes are L-shaped and end with the inner surface of their vertically upward-pointing tab at the edge of overflow opening 31. Their horizontally oriented tab is located closely below the edge of the opening of inlet tube 17.

Collecting tank 36 which has the shape of a cylindrical cup is detachably fastened to the lower end of centrifuge drum 26, with sealing ring 37 inserted and in such a manner that it cannot rotate relatively to said drum. In order to establish a detachable fastening which prevents relative rotation, several, for example four, bayonet locks are provided along the periphery, with two bayonet pins attached to peripheral wall 27 of the drum being visible in FIG. 1. The bayonet pins 38 cooperate with bayonet slots 39 located in the edge area of collecting tank 36, with one of these slots being shown in FIG. 10. Collecting tank 36 is attached to the centrifuge drum by pushing the bayonet slots with their slot section opening toward the top onto the bayonet pins 38 until the bayonet pins reach the horizontal part of the bayonet slots. The bayonet lock is then locked by rotating collecting tank 36 to the left until the bayonet pins can enter the shorter sections of the slot which point in the vertical direction and are closed at the top. After collecting tank 36 has been moved slightly downwards it is attached to centrifuge drum 26 in such a way that it cannot rotate relative to the latter.

The left half of FIG. 1 shows collecting tank 36 and the transport container 21 which surrounds it on all sides without touching it, in the position they have when the centrifuge is operating. The right half of FIG. 1 shows, on the other hand, the relative positions of transport container 21 and collecting tank 36 during the operation to be described below in which both containers are jointly detached from the device. Here transport container 21 is shown in the raised position.

Transport container 21 is detachably fastened to housing 10, also by means of a bayonet lock. For this purpose several bayonet pins 40 are attached in the embodiment shown to the periphery of transport container 21 which engage bayonet slots 41 provided in ring-shaped wall 19. The shape of the bayonet slots 41 is shown in FIG. 9. When transport container 21 is attached to housing 10, the bayonet pins 40 first enter the shorter sections of the bayonet slot, which are open toward the bottom, one of which is shown on the left side of FIG. 9. Now transport container 21 is lifted until the bayonet pins 40 reach the longer of the two horizontal slot sections. When the transport container is rotated toward the right the bayonet pins 40 move in this horizontal part of the slot until they reach the catch recesses 42 one of which is shown in FIG. 9. In this position transport container 21 is held in a fixed position relative to housing 10 by the bayonet pins 40 which engage the catch recesses 42 and form, together with said catch recesses 42, a lock against rotation. The rotational lock can be released by slightly lifting and turning the transport container 21.

In order to be able to detach transport container 21 and collecting tank 36 jointly from housing 10, it is necessary to have both containers engage each other in such a manner that they cannot rotate against each other. At least one stop 50 is provided for this purpose on collecting tank 36 and at least one counterstop 51 on transport container 21 is associated with it. When transport container 21 is lifted into the position shown in the right half of FIG. 1, stop 50 and counterstop 51 are engaging each other in such a manner that when the two containers are rotated toward the right they are simultaneously released from the bayonet lock in question.

If the two containers are to be removed, transport container 21 is first, by rotation to the right, moved from its rotary catch position. By this movement the bayonet pins 40 are removed from the corresponding catching recesses of the bayonet slots 41. The rotation of the transport container 21 toward the right is continued until the bayonet pins 40 are located opposite the vertical short slot sections at the center, which connect the two horizontal slot sections of the bayonet slots 41 with each other. Now transport container 21 is lifted, with the bayonet pins 40 moving upwards in the corresponding short sections of the slots. During this operation stop 50 and counterstop 51 become engaged. In the last phase of the upwards motion, collection tank 36 is taken along in the upward direction, with its bayonet slots 39 being shifted upwards in relation to the stationary bayonet pins of centrifuge drum 26. At the end of the upward motion of the two containers 21 and 36 the bayonet pins 40 and 38, respectively, associated with each container, are located opposite horizontal slot sections. When transport container 21 and collecting tank 36, connected to it in such a manner that relative rotation is excluded, are rotated further toward the right, the bayonet pins 38 and 40 finally move into the vertical slot sections which are open toward the top and the bottom, respectively, and the two containers can then be jointly pulled off downwards.

For closing transport container 21 there is provided cover 52 comprising at its edge bayonet slots 53 which are designed in such a manner that they can engage the bayonet pins 40. The engagement is arranged in such a way that cover 52 which has been placed on top [of the container] and locked in place sits tightly on lip seal 22. For storing cover 52 on transport container 21 when the cover is not in use, bayonet pins 54 are provided on the outside of the transport container near the bottom which cooperate with the bayonet slots 53.

In order to describe in detail the barrier means which prevent clean water from penetrating from discharge space 14 into the gap-shaped part of the housing which adjoins the housing periphery of peripheral wall 27 of the drum and is indicated by reference numeral 55, we are now referring to FIG. 1 together with FIGS. 5 to 8. The gap-shaped housing space 55 is in communication with the gap-shaped space between transport container 21 and collecting tank 36. In order to establish a barrier it is provided in all embodiments that the cylindrical inside surfaces of casing wall 18 continue in and are in line with a closed ring-shaped wall 56 or 56', respectively, which extends toward the top into discharge space 14 up to a point closely below barrier flange 30 of centrifuge drum 26. In the left half of FIG. 1 and in the embodiments according to FIGS. 5, 7 and 8 an additional ring-shaped wall 57 is provided in addition to ring-shaped wall 56 at a radial distance from ring-shaped wall 56. Ring-shaped wall 57 extends upwards from bottom 58 of discharge space 14 and also ends closely below barrier flange 30. Ring-shaped wall 56' shown in the right half of FIG. 1 is designed as a ring-shaped wall with external steps, as is the embodiment shown in FIG. 6.

At least one circle of radial vanes extending downwards is fastened to barrier flange 30. In the embodiment according to the left half of FIG. 1, which is very similar to the embodiment according to FIG. 5, two sets of vanes 59 and 60 or 60', respectively, are provided. In the embodiment according to the right half of FIG. 1, which corresponds to the embodiment according to FIG. 6, only one set of vanes 61 is attached to barrier flange 30, with the vanes 61 being designed with steps matching ring-shaped wall 56'. In the embodiment according to FIG. 7 two sets of vanes are provided in principle; the vanes extend, however, downwards from a transverse part with which they form one piece and which extends as far as the peripheral drum wall 27. All the vanes according to FIG. 7 are given the reference numeral 62. The ring-shaped walls 56, 56' and 57 and the vanes 59 to 62 are in each case in such a position relative to each other that narrow gaps are formed between them.

The ring-shaped walls 56, 56' and 57 ensure that water which is still present in discharge space 14 when the centrifuge is standing still cannot penetrate into housing space 55 or between the walls of the two containers 21 and 36. When the centrifuge is in operation the vanes 59 to 62 form a dynamic seal because they ensure that the clean water emerging from the centrifuge is moved radially outward by centrifuge drum 26.

FIG. 7 shows that peripheral wall 27 of the drum can be covered on the inside with a coating 63 protecting it against wear.

FIGS. 11 to 14 show how an infrared light sensor can be provided for indicating the filling level in collecting tank 36. For this purpose two diametrically opposed channels 64 which are directed inwards and have identical dimensions are provided in collecting tank 36. In the position of the parts shown in FIG. 11 IR light source 65 is positioned opposite one channel 64 and IR sensor 66 is positioned opposite the other channel 64. Light source 65 and sensor 66 are fastened to centrifuge frame 67 in a suitable manner so that they are stationary. Their joint optical axis is directed toward the channels 64, i.e. it intersects the centerline of the device. The entire collecting tank 36 and the entire transport container 21 may consist of material which is transparent to infrared light. It is, however, sufficient if the opposed surfaces of the channels 64 on collecting tank 36 as well as the areas of the wall of transport container 21 which are located opposite light source 65 and sensor 66 are transparent to IR light.

It is also possible to measure the filling level by measuring the starting torque of motor 23, because said starting torque is a function of the mass of the solid particles in collecting tank 36. The curve of the torque during the start of motor 23 can be monitored by suitable electronic means and when a limit is exceeded an optical and/or acoustic signal can be triggered which indicates that the maximum filling level in the collecting tank has been reached.

The device according to the invention functions as follows:

The waste water from a dentist's office carrying solids flows into centrifuge 11 through intake fitting 13, intake duct 12 and inlet tube 17. It is then carried along by the guiding vanes 33 and transported along the vanes 33 to the inner surface of peripheral wall 27 of the drum. While this takes place, the solids are deposited, as is usual in such centrifuges, at the peripheral wall of the drum, while the water, because of its lower density, remains on the inside, closer to the axis of rotation. The ring-shaped layer of water grows toward the interior until it reaches the outside diameter of the overflow opening 31. Clean water from which the solid particles have been removed then flows continually through overflow opening 31 into discharge space 14 and is made to flow outwards by barrier flange 30 rotating with centrifuge drum 26. During this action the barrier means 32, 32' and 32", respectively, provide a dynamic seal between the space for the clean water and housing space 55.

When the centrifuge is shut down, the deposited solids slide downwards along the peripheral drum wall 27 under the influence of gravity and continue their slide path on the conical inner surface of drum bottom 28, until they pass through orifice 29 into collecting tank 36. The separated solids discharged into collecting tank 36 and the water which has flowed into collecting tank 36 form two separate layers when the centrifuge is operating, with the solids being, of course, deposited at the wall of collecting tank 36, while the ring of water builds up in the inward direction toward the center of rotation, until the excess water can again flow through orifice 29 into centrifuge drum 26 from where it is directed, in the manner described above, as clean water into discharge space 14 through overflow opening 31. If the layer of solids which contains only little residual moisture and is deposited in collecting tank 36 reaches a thickness exceeding the radial dimensions of the channels 64, the light emitted by light source 65 can no longer be received by sensor 66, and a signal is triggered.

When the two bayonet locks of containers 21 and 36 are loosened, provision must, of course, be made to have centrifuge drum 26, and consequently its bayonet pins 38, held in place, so that relative rotations of the containers against the bayonet pins 38 are possible. This can be accomplished by suitable mechanical anti-rotation means acting on the centrifuge drum 26, but also by electrical braking of electric motor 23.

The channels 64 required for the electric eye and sensor do not have to have the shape shown in FIGS. 11 to 13. It is quite sufficient if channels 64' according to the embodiment shown in FIG. 14 are designed similar to cylindrical bushings and are inserted at diametrically opposed points into the wall of collecting tank 36. In this case, too, the opposing front surfaces of the channels must consist of material that is transparent to infrared light.

For the explanation of the device which can, in addition, separate a liquid/gas/solids mixture into its three phases we are referring below to FIGS. 15 to 21.

In the embodiment of FIG. 16 the cross sections shown in FIGS. 17, 18 and 19 were also made along lines identical with the corresponding lines in FIG. 15.

The device shown in FIG. 15 comprises a housing indicated by reference numeral 10, which consists of lower housing 10a and upper housing 10b which is joined to the lower housing in a manner known per se to form a rigid and tight connection. A centrifuge indicated by the reference numeral 11 is located in lower housing 10a.

Intake fitting 13 is attached to intake duct 12 for waste water containing solids which is fed to the device from, for example, the cuspidor bowl of a dental treatment unit, with said intake duct being transverse to the centerline of the device. Below intake duct 12 there is located the ring-shaped discharge space 14 for the clean water coming from centrifuge 11, with said discharge space being connected to discharge duct 43 for clean water to which discharge fitting 15 is connected. As shown in FIG. 19, intake duct 12 leads tangentially into inlet chamber 16 which is concentric with the centerline of the device and to which is connected an inlet tube leading downwards. Inlet tube 17 forms the inside limit of ring-shaped discharge space 14 and reaches into casing wall 18 of housing 10, which casing is concentric with the centerline of the device and essentially encloses centrifuge 11.

Adjoining casing wall 18 is exterior ring-shaped wall 19 which extends further downwards and forms the outside limit of receiving space 20 opening toward the bottom. The upper end of cylindrical transport container 21 extends into receiving space 20. Said container is by means of a screw or bayonet connection detachably fastened to ring-shaped wall 19 and which is, in the position in which it is shown to be attached in FIG. 15, sealed against lower housing 10a by sealing ring 22.

Electric motor 23 is fastened to upper housing 10b by means of a flange in such a way that its principal axis is in line with the centerline of the device. Drive shaft 24 of electric motor 23 passes through housing seal 25 and extends through both upper housing 10b and lower housing 10a. Drive shaft 24 carries the centrifuge drum of centrifuge 11, which drum is referred to as a unit by reference numeral 26 and is attached to said shaft in such a manner that it cannot rotate in relation to it. Centrifuge drum 26 comprises a cylindrical peripheral drum wall 27 and a conical drum bottom 28 adjoining said wall at the bottom with said drum bottom ending in central orifice 29. Said orifice is of circular shape and concentric with the centerline of the device.

At the free end of the peripheral wall 27 of the drum there is located barrier flange 30 in the shape of a circular ring whose central opening forms the limit of overflow opening 31, also in the shape of a circular ring, whose inner limit is formed by the external surface of inlet tube 17. Barrier flange 30 extends radially toward the outside from the peripheral wall 27 of the drum, in order to permit positioning of the barrier means generally referred to under the reference numeral 32.

Centrifuge drum 26 is rigidly connected through a plurality of radially directed spoke-like arranged vanes 33 with hub sleeve 34 which is placed on drive shaft 24 and fastened to the latter by means of threaded bolt 35 in such a manner that centrifuge drum 26 and all parts rigidly attached thereto are carried by drive shaft 24 in such a manner that they cannot rotate in relation to said shaft. Hub sleeve 34 extends as far as the flange of electric motor 23 and is sealed by housing seal 25 against upper housing 10b. The vanes 33, in the embodiment shown in the drawing four vanes arranged in the form of a cross (FIG. 20), extend between the inner surface of peripheral wall 27 of the drum and hub sleeve 34, as shown in FIGS. 15 and 20. Although the section runs through a center plane of the device according to FIG. 15, the vanes 33, which would normally also be shown cut, are shown without being cut in order to more clearly demonstrate the design and the function of the device. Further details of the design of the blades 33 will be explained below.

Threaded bolt 35 comprises collar 44 from the middle of which collar threaded stud 45 extends upwards and threaded stud 46 downwards, both of them in concentric locations. Threaded stud 45 engages interior thread 47 at the lower end of drive shaft 24 and fastens by means of the contact between the collar and the lower face of hub sleeve 34 said hub sleeve and all parts rigidly attached to it to drive shaft 24 which engages hub sleeve 34 in the area of threaded stud 35 in such a manner that it cannot rotate in relation to said hub sleeve. Collecting tank 36 in the shape of a cylindrical cup comprises central stud 48 which points upwards and has an internal thread 49 which is used to screw collecting tank 36 to threaded stud 46. When collecting tank 36 is screwed onto threaded stud 46, sealing ring 37 is placed between ring-shaped shoulder 68 of collecting tank 36, which shoulder protrudes toward the inside, and the corresponding ring-shaped surface 69 of centrifuge drum 26. This action seals collecting tank 36 which extends with its upper end beyond the lower part of circumferential wall 27 of the drum, against centrifuge drum 26.

After collecting tank 36 has been screwed to centrifuge drum 26 in the manner described above, these two elements form a rotational unit which can be rotated by the action of drive shaft 24. If collecting tank 36 which is filled with separated solids up to a preestablished level is to be emptied or replaced, said collecting tank 36 is unscrewed by suitable relative rotation in relation to the centrifuge drum which is held stationary by suitable means. Collecting tank 36 which has been unscrewed and is filled with solids is placed into transport container 21 which has previously been detached by unscrewing of screw joint 40 and for whose closing cover 52 is provided. Cover 52 is attached to the lower end of transport container 21 by a screw connection 53 or by means of a bayonet-type fastening. Screw joint 53 or the corresponding bayonet-type fastening is compatible with the corresponding screw joint 40 or the corresponding bayonet-type fastening, so that cover 52 for closing transport container 21 can be attached to the top of the latter, with sealing ring 22 ensuring the seal between transport container 21 and cover 52.

When cover 52 is not in use, it is in the position at the bottom of transport container 21 shown in FIG. 15.

The barrier means 32 prevent clean water from penetrating from discharge space 14 into the gap-shaped housing space which adjoins the periphery of peripheral wall 27 of the drum and is indicated by reference numeral 55. The gap-shaped housing space 55 is in communication with the gap-shaped space between transport container 21 and collecting tank 36. Ring-shaped wall 56 concentrically adjoins mantle wall 18, which limits gap-shaped space 55 on the outside, in such a manner that it is in line with the continuous interior hole and extends upwards into discharge space 14 to a point closely below barrier flange 30 of centrifuge drum 26. Ring-shaped wall 56 comprises radial steps on the outside with said steps matching the vanes 61 which have a corresponding shape and are placed in a wreath-like arrangement on the underside of barrier flange 30. In this arrangement the blades 61 and the ring-shaped wall comprising steps are positioned in such a manner relative to each other, that the gaps between them are narrow. Ring-shaped wall 56 ensures that clean water that still remains in discharge space 14 when the centrifuge is standing still cannot enter housing space 55. When the centrifuge is running the vanes 61 act as a dynamic seal because they ensure that the clean water coming from the centrifuge is transported radially outwards. The barrier means 32 can, of course, also have different shapes, as shown and explained in FIGS. 1 and 5 to 18. It is also possible, if collecting tank 36 is designed accordingly, to provide a level indicator device, for example an electric eye system sensitive to infrared, as described with reference to FIGS. 11–14. The design of the device of FIGS. 15–21 differs from the embodiment described with reference to FIG. 1 in that the radial distance of inlet tube 17 from drive shaft 24 or from hub sleeve 34 is large enough to permit the placement of suction tube 70 and separating tube 71, for the purpose described in more detail below, between drive shaft 24 and inlet tube 17.

Suction tube 70 is attached to the upper housing 10b concentrically to drive shaft 24 and protrudes enough from said housing that, when housings 10a and 10b are joined, it extends into centrifuge drum 26. Suction tube 70 limits suction space 72 surrounding drive shaft 24 or hub sleeve 34, respectively, and is, at its upper end, connected to suction duct 73 which leads tangentially into suction space 72, as shown in FIGS. 15 and 17. Suction fitting 74, which can be connected to a source of reduced pressure, is connected to suction duct 73.

Between inlet tube 17 and suction tube 70 there is placed separating tube 71 concentrically thereto which encloses suction tube 70 within lower housing 10a in such a manner that ring-shaped space 75 is formed. By means of the guiding vanes 33, separating tube 71 is fastened to centrifuge drum 26 in such a manner that it cannot rotate relative to the latter. At its open upper end separating tube 71 is connected with intake duct 76 for a liquid/gas/solids mixture, which duct is located in upper housing 10b. For this purpose the upper end of separating tube 71 is inserted into a cylindrical hole 77 which is concentric with it and in which is placed sealing ring 78 which seals intake ducts 12 and 76 from each other and which, because of the rotation of separating tube 71, has the properties of a slip ring. Intake duct 76 leads tangentially into ring-shaped space 75 between suction tube 70 and separating tube 71, as shown in FIG. 15 combined with FIG. 18. Fitting 79 is attached to intake duct 76 and is used to connect same with a waste water feeding line, for example the discharge line from the cuspidor bowl. Separating tube 71 forms the inner limit of inlet chamber 16 for the waste water, through which chamber it passes coaxially.

The lower end of separating tube 71 carries an annular separating flange 80 which extends outwards and is very important for the functioning of the device. When the centrifuge is in operation, separating flange 80 dips with its entire periphery into liquid layer 81 which forms at peripheral wall 27 of the drum. Separating flange 80 which dips into liquid layer 81, i.e. the water ring of the centrifuge, approximately at a point close to the transition between peripheral wall 27 of the drum and conical drum bottom 28, and which can therefore be located somewhat lower than shown in FIGS. 15 and 16, divides the layer of liquid into an upper area and a lower area. These two areas can, however, communicate with each other underneath separating flange 80, because the peripheral surface of said separating flange ends radially in front of peripheral wall 27 of the drum.

In the ring-shaped space 75 between suction tube 70 and separating tube 71 there are located several acceleration vanes 33a at equal angular distances from each other, which are attached to separating tube 71 and end in the radial direction at a distance from suction tube 70, as can be seen from FIG. 15 in combination with FIG. 19. Four accelerating vanes are provided in the example shown which are designed so that each forms one piece with the guiding vanes 33. The lower edges of the guiding vanes 33 are located approximately at the transition point between the peripheral wall 27 of the drum and the conical drum bottom 28. Their upper edges end in different horizontal planes. On the inside, at the hub sleeve 34, the adjoining upper edge of the guiding vanes 33 are located below the lower face of suction tube 70, without making contact. On the outside of peripheral wall 27 of the drum the guiding vanes 33 end below the lower face of inlet tube 17, without making contact. On the outside of separating tube 71 upwards-pointing noses 33b of the guiding vanes 33 extend into inlet chamber 16 and end radially in front of the inner surface of inlet tube 17. The guiding vanes 33 and the accelerating vanes 33a and noses 33b, which are in one piece with the vanes 33, are attached to peripheral wall 27 of the drum, separating tube 71 and hub sleeve 34, which provides for connection of all the parts which rotate when the centrifuge is operating. This connection is such that the above parts cannot rotate relative to each other.

FIG. 15 shows that inlet duct 12, outlet duct 43, inlet duct 76 and suction duct 73 are located one above the other in different planes and all end at the same side of the device, which makes it easier to connect the device to the corresponding lines and contributes to the compact design of the device. The ducts and the fittings connected to them may be arranged somewhat twisted relative to the axis of rotation, in order to facilitate the connection of the outside lines.

The embodiment shown in FIG. 16 differs from that of FIG. 15 only in that no transport container 21 is provided for collecting tank 36. Accordingly the casing wall 18 of lower housing 10a ends at the bottom in a plane surface without a protruding ring-shaped wall 19.

The device described in relation to FIGS. 15 to 21 operates as follows:

The waste water generated by dental activities which carries solids, and flows through intake fitting 13 and intake duct 12 into inlet chamber 16, is taken up, in inlet tube 17 which forms the lower part of inlet chamber 16, by the noses 33b of the guiding vanes 33 and finally by the guiding vanes 33 themselves and transported under the influence of the centrifugal force along the guiding vanes 33 to the inner surface of peripheral wall 27 of the drum. The solids are deposited here at the peripheral wall of the drum, as is usual in such centrifuges, while the water, because of its lower density, remains further to the inside, relative to the axis of rotation, and forms liquid layer 81 into which separating flange 80 is dipping. The ring-shaped layer of water builds up toward the inside until it reaches the outside diameter of overflow opening 31. Clean water, from which the solid particles have been removed then flows continually through overflow opening 31 into discharge space 14 and is directed outwards by barrier flange 30 which rotates with centrifuge drum 26. In this process the barrier means 32 ensure dynamic sealing of the cleanwater space from housing space 55. In this respect the operation of the device corresponds to that according to FIGS. 1 to 8.

If, during the operation of the centrifuge described above, a source of reduced pressure is activated which is effective through suction fitting 74, suction duct 73 and suction space 72, reduced pressure is created in the interior of the centrifuge drum and, of course, also in the interior of collecting tank 36, which reduced pressure can, because of the sealing effect of separating flange 80 which dips into liquid layer 81, not be effective in the spaces of the device which are located above separating flange 80. The reduced pressure makes it possible, through connecting fitting 79 and intake duct 76, to suck from the mouth of the dentist's patient the mixture of liquids, solids and gases which is to be separated. In ring-shaped space 75 the mixture is taken up by the acceleration vanes 33a. As a result of the centrifugal force which is effective there the gaseous phase is separated from the other two phases, with the gas flowing downwards inside the ring-shaped space along the outer surface of suction tube 70, while the solids and the liquid move outwards to the inside wall of separating tube 71 and there flow downwards under the influence of gravity. This process can be further improved by an acceleration of the flow which is obtained by designing ring-shaped space 75 in such a manner that it continually gets smaller in the downward direction, which can be ensured by appropriate conical design of suction tube 70 and/or separating tube 71 or of the wall surfaces of these pipes which form the limits of ring-shaped space 75 (not shown).

After having been deflected by 180° at the end of ring-shaped space 75 along the bottom face of suction tube 70, the separated gas flows upwards through suction space 72 and is discharged through suction duct 73 and suction fitting 74. Because of the cyclone effect at this point, drops of liquid which are being carried along by the gas are separated where the gas flow is deflected and carried outwards in the direction of wall 71 of the separating tube. FIG. 15 shows that the suction tube 70 ends at a distance from separating flange 80.

The liquid/solids mixture remaining after the gas has been separated flows outwards along separating flange 80 and arrives in liquid layer 81 in which, because of the centrifugal effect, the solids are separated in the direction toward the peripheral wall 27 of the drum. The cleaned liquid flows upwards past the peripheral surface of separating flange 80, flows over barrier flange 30 which protrudes in a weir-like manner, and is discharged through overflow opening 31.

When the centrifuge is shut off, the ring of water disappears and pressure equalization takes place above separating flange 80. The solids deposited at the peripheral wall 27 of the drum slide downwards along the peripheral wall of the drum as a result of gravity, continue sliding on the conical interior surface of the drum bottom 28 and pass through orifice 29 into collecting tank 36, as has been described above. The solids that have moved into collecting tank 36 and the water moving into collecting tank 36 form, while the centrifuge is in operation, two separate layers on the outer wall of collecting tank 36, with the solids, because of the action of the centrifugal force and their greater density, being deposited on the wall of collecting tank 36, while a ring of water builds up in the inward direction toward the center of rotation, which can increase in thickness until excess water can again flow to the centrifuge drum through orifice 29. From there it follows the path, described above, through overflow opening 31 into the discharge space for clean water. The level indicator described above responds to the thickness of the solids layer deposited in collecting tank 36 and signals that collecting tank 36 must be replaced or emptied.

The device shown in FIGS. 15 and 16 can be modified in accordance with FIG. 21. Here the suction tube 70 is, in the area of intake duct 76, closely, i.e. with a small gap, surrounded by enveloping tube 82 which, at its exterior peripheral surface is rigidly connected with the acceleration vanes 33a and therefore participates in the rotation of the centrifuge. Enveloping tube 82 ends at the upper ends, without touching it, at a distance from the wall surface of the housing 10b which forms the limit of inlet duct 76 from above, and reaches with its lower end into ring-shaped space 75.

In this design of the device the sucked-in liquid/gas/solids mixture does not, as it does in FIGS. 15, 16 and 18, make contact with the stationary, i.e. non-rotating, suction tube 70, but with enveloping tube 82 which rotates with the same speed as the centrifuge. As a result, the solids and also the liquid contained in the mixture are flung outwards, away from the axis of rotation, by separating tube 82. As a result these phases of the mixture can definitely not flow downwards along the exterior peripheral wall of the stationary suction tube 70, so that parts of these phases cannot be carried along into suction space 70 during the 180° deflection which takes place at the lower face of suction tube 70.

We claim:

1. Device for separating fine solid particles from waste water, in particular amalgam particles from the waste water of a dentist's office, comprising:
a centrifuge drum surrounding by a housing, the drum having a peripheral wall, a conic drum bottom having a central orifice and being connected to the drum wall so as to project downwardly and a ring-shaped barrier flange carried by the upper free end of the peripheral wall of the drum so as to extend radially inwardly and form a limit of an overflow opening through which the inside of the centrifuge drum communicates with a discharge space for clean water, which space is located in said housing, a drive shaft of a motor attached to the housing, which drive shaft carries the centrifuge drum, an inlet tube which surrounds the drive shaft concentrically at radial distance, is firmly attached to the housing, passes through the overflow opening with radial play and communicates with a duct located in the housing for intake of waste water, and with the interior space of the centrifuge drum, and a detachably attached collecting tank for the separated solid particles which communicates through the orifice with the interior space of the centrifuge drum, wherein the collecting tank (36) is detachably and in a sealed manner attached to the centrifuge drum (26) in such a manner that it cannot rotate relative to same, the barrier means (32, 32', 32") being provided with separate housing space (55) adjoining the external periphery of the peripheral wall (27) of the drum from the discharge space for clean water.

2. Device according to claim 1, wherein the collecting tank (36) is placed within a transport container (12) which surrounds the collecting tank (36), except when the latter is being replaced, so as not to touch it and which is attached to the housing (10) by its opening in a sealed and detachable manner.

3. Device according to claim 2, wherein the centrifuge drum (26) and the collecting tank (36) are connected to each other by a first bayonet lock which is unlockable by lifting and rotating the collecting tank (36).

4. Device according to claim 3, wherein the transport container (21) is attached to the housing (10) by means of a second bayonet lock (40, 41) which can be unlocked, together with the first bayonet lock (38, 39) connecting centrifuge drum (26) with collecting tank (36), by lifting it and subsequently rotating it with the transport container (21) and the collecting tank (36) being in engagement with each other after the transport container has been lifted.

5. Device according to claim 4, wherein the second bayonet lock (40, 41) of transport container (21) comprises a catch (42) which must be released before transport container (21) can be rotated into a position permitting lifting.

6. Device according to claim 5, wherein the transport container (21) with the collecting tank (36) being inside is closeable by a cover (52) which comprises at its edges bayonet elements (53) which engage bayonet elements (40) of the second bayonet lock provided on the transport container and that said cover can, when not in use, be attached on the outside to the bottom of the transport container (21), with its bayonet elements (53) engaging corresponding bayonet elements (54) provided next to the bottom of the transport container (21).

7. Device according to claim 6, wherein a seal (22) is attached to the opening of the transport container (21) which seal, when the transport container is attached to the housing (10), makes contact with a sealing surface of the housing and, when the cover (52) is attached to the transport container (21), makes contact with the cover.

8. Device according to claim 1, wherein the barrier means (32, 32', 32") includes at least one closed ring-shaped wall (56) which is concentric with the centrifuge drum (26) and protrudes upwards from the bottom surface (58) of the discharge space (14) for clean water, and at least one circle, also concentric with the centrifuge drum (26), of vanes which are radially oriented and adjoin the ring-shaped wall in such a manner that a narrow gap is formed, the barrier flange (30) also extending radially outwards from the peripheral wall (27) of the drum beyond the ring-shaped wall (56), of which at least one is present, and that the vanes (60) are attached to the barrier flange (30) in such a manner that they protrude downwards.

9. Device according to claim 8, wherein two ring-shaped walls (56, 57) and two circles or vanes (59, 60) which engage them are provided.

10. Device according to claim 8, wherein one ring-shaped wall (56') is provided which comprises steps on the outside thereof and vanes (61) with a corresponding step shape are also provided.

11. Device according to claim 8, wherein the vanes (62) extend to the peripheral wall (27) of the drum.

12. Device according to claim 1, wherein at least two channels (64) are provided on the collecting tank (36) which are positioned opposite each other in pairs, are directed inwards, have identical dimensions and consist of material which is transparent to light, that, if desired, the transport container (21) is transparent to light in at least two areas located opposite each other and that, in a manner known per se, a light-sensing system (65, 66) is fastened to the frame (67) of the centrifuge for the purpose of determining the filling level, with the optical axis of said light-sensing system being lined up with said channels (64).

13. Device according to claim 1, wherein the starting torque of the motor (23) is measured in order to determine the filing level of the collecting tank (36).

14. Device according to claim 1, wherein the inside radius of the collecting tank (36) is greater than the inside radius of the peripheral wall (27) of the drum.

15. Device according to claim 1, wherein a suction tube (70) is provided concentrically with the drive shaft (24) and permanently attached to the housing, whose lower open end extends into the centrifuge drum (26) and forms the limit of a suction space (72) surrounding the drive shaft (24), which space can be connected to a source of reduced pressure, a separating tube (71) is provided between the suction tube (70) and the inlet tube (17) and concentrically to them, which is located in the housing (10) and attached to the centrifuge drum (26) in such a manner that it cannot rotate relative to the latter, whose upper open end communicate with the intake duct (76) for a liquid/gas/solids mixture, whose lower open end extends into the centrifuge drum and which forms, together with the suction tube (70), a ring-shaped space (75), the upper end of the separating tube (71) passes rotatably through a sealing ring (78) fastened to the housing (10) which seals the intake duct (12) for waste water against the intake duct (76) for liquid/gas/solids mixtures, and the separating tube (71) comprises at its lower end a separating flange (80) extending outwards which, when the centrifuge is in operation, dips with its entire periphery into a liquid layer (81) formed on the peripheral wall (27) of the drum.

16. Device according to claim 15, wherein suction tube (70) communicates at its upper end with a suction duct (73) tangentially connected to the suction space (72).

17. Device according to claim 16, wherein the intake duct (12) for waste water, one discharge duct (43) for clean water, the suction duct (73) and the intake duct (76) for the liquid/gas/solids mixture all lead, one above the other, to one side of the device.

18. Device according to claim 15, wherein several acceleration vanes (33a) are provided at equal angular distances from each other in a ring-shaped space (75) between the suction tube (70) and the separating tube (71), which vanes are attached to the separating tube (71) and extend radially to a point at a distance from the suction tube (70).

19. Device according to claim 18, wherein the intake duct (76) for the liquid/gas/solids mixture is tangentially connected to the ring-shaped space (75) between the suction tube (70) and the separating tube (71).

20. Device according to claim 18, wherein the accelerating vanes (33a) are made in one part with guiding vanes (33) which connect the centrifuge drum (26) with a hub sleeve (34) placed on the shaft (24) in such a manner that these parts cannot rotate in relation to each other.

21. Device according to claim 18, wherein the suction tube (70) in the area of the intake duct (76) for the liquid/gas/solids mixture is closely surrounded by an enveloping tube (82) whose lower end extends into the ring-shaped space between the suction tube (70) and the separating tube (71) and is connected through the accelerating vanes (33a) with the separating tube (71) in such a manner that it cannot rotate in relation to the latter.

22. Device according to claim 18, wherein the ring-shaped space (75) is designed in such a manner that between the suction tube (70) and the separating tube (71) its cross section continually decreases in the flow direction of the liquid/gas/solids mixture.

23. Device according to claim 15, wherein the intake duct (12) for waste water is tangentially connected to a ring space-shaped inlet chamber (16) whose outside limits are formed by the housing (10a) and the inlet tube (17).

24. Device according to claim 20, wherein the inside limits of inlet chamber (16) are formed by the separating tube (71) which passes through it coaxially.

25. Device according to claim 15, wherein the separating flange (80) dips into the liquid layer (81) approximately in the vicinity of the transition between the peripheral wall (27) of the drum and the conical drum bottom (28) and divides said layer into two sections which communicates with each other below the separating flange (80) ending radially at a distance from the peripheral wall (27) of the drum.

26. Device according to claim 23, wherein the housing (10) is composed of a lower housing (10a) and an upper housing (10b), with the lower housing (10a) comprising the inlet chamber (16) for waste water, the inlet tube (17), the intake duct (12) for waster water, the discharge space (14) for clean water and the centrifuge drum (26) with the separating tube (71), while the housing (10b) comprises the suction duct (73), the intake duct (76) for the incoming liquid/gas/solids mixture and the suction tube (70) protruding therefrom, and the drive shaft (24) and the hub sleeve (34) pass through the upper and lower housings (10b, 10a), with the hub sleeve (34) passing through a housing seal (25) in the upper housing (10b), which seals off the reduced pressure from the outside.

* * * * *